United States Patent [19]

Davenport

[11] Patent Number: 5,400,781

[45] Date of Patent: Mar. 28, 1995

[54] CO2 GAS SAMPLING MASK HAVING A BEVELLED SAMPLING TUBE EXTENDING INTO THE MASK

[76] Inventor: Richard A. Davenport, 501 Washington Dr., Lebanon, Tenn. 37087

[21] Appl. No.: 277,932

[22] Filed: Jul. 20, 1994

Related U.S. Application Data

[63] Continuation of Ser. No. 101,586, Aug. 3, 1993, abandoned.

[51] Int. Cl.$^6$ ............................................. A62B 18/02
[52] U.S. Cl. ........................... 128/206.28; 128/206.21; 128/205.25
[58] Field of Search ............... 128/202.27, 205.25, 128/206.21, 206.24, 206.28

[56] References Cited

U.S. PATENT DOCUMENTS

| | | | |
|---|---|---|---|
| 1,926,027 | 9/1933 | Biggs | 128/206.22 |
| 2,248,477 | 7/1941 | Lombard | 128/205.25 |
| 2,625,155 | 1/1953 | Engelder | 128/206.24 |
| 2,795,223 | 6/1957 | Stampe | 128/730 |
| 3,395,701 | 8/1968 | Bartlett, Jr. | 128/202.22 |
| 4,201,205 | 5/1980 | Bartholomew | 128/205.25 |
| 4,258,710 | 3/1981 | Reber | 128/204.13 |
| 4,328,797 | 5/1982 | Rollins, III et al. | 128/206.24 |
| 5,005,571 | 4/1991 | Dietz | 128/205.25 |
| 5,046,491 | 9/1991 | Derrick | 128/200.24 |

Primary Examiner—Kimberly L. Asher
Attorney, Agent, or Firm—Edward D. Lanquist, Jr.

[57] ABSTRACT

An oxygen mask made of clear flexible material, for example, polyvinyl chloride, has a gas pocket just inside two holes in it, below the nose and in front of the mouth, the holes adapted to lead via tubing, one to an oxygen source and the other to a respiratory gas or carbon dioxide monitor, the rest of the mask being gas-proof except for permissible small openings at about ear and cheek level. The gas pocket is formed by the mask extending outward in front of the face, particularly the nose and mouth, and having the holes in the floor thereof, tubes and connectors being adapted to fit through the holes and go to an oxygen source and a carbon dioxide monitor.

6 Claims, 1 Drawing Sheet

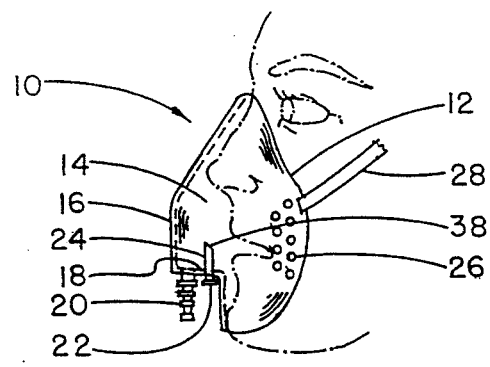
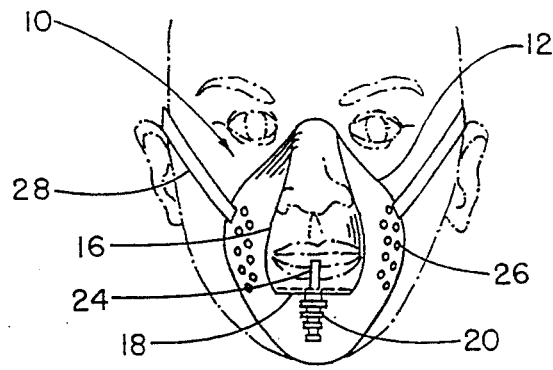
FIG 1
FIG 2
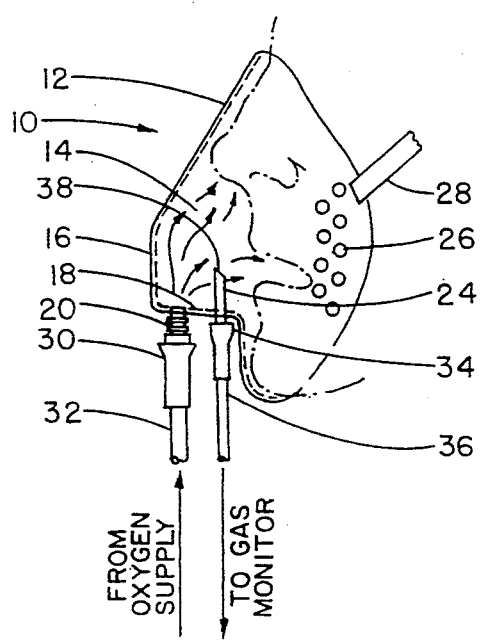
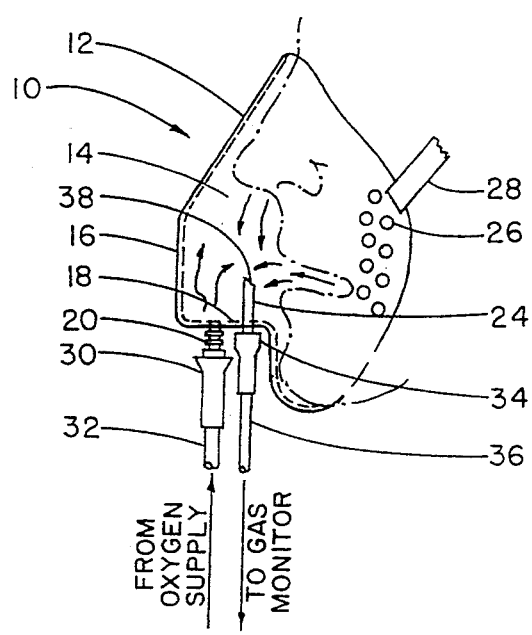
FIG 3
FIG 4

CO₂ GAS SAMPLING MASK HAVING A BEVELLED SAMPLING TUBE EXTENDING INTO THE MASK

This application is a continuation of application Ser. No. 08/101,586, filed Aug. 3, 1993, now abandoned.

BACKGROUND OF THE INVENTION

1. Field of the Invention

This invention relates to an oxygen mask. More particularly, it relates to an oxygen mask having an opening for oxygen intake and an opening for exhaled or discharged gases, often called respiratory gases.

2. Description of the Prior Art

For years research has been going on on how to monitor oxygen intake and carbon dioxide outake of a patient safely, comfortably and easily while he or she is under anesthesia. For example, U.S. Pat. No. 1,926,027 describes a breathing apparatus which has a tubular connection 3 with a relief port 4. U.S. Pat. No. 2,248,477 concerns an inhalator mask which has an inner chamber in gaseous communication with an outer chamber. U.S. Pat. No. 2,795,223 describes apparatus made up of a tube having a mouthpiece, the tube also having a by-pass duct communicating with a chamber. In U.S. Pat. No. 4,201,205 is disclosed use of non-elastic flexible tubing which extends over and around the user's ears and under his chin. U.S. Pat. No. 4,258,710 involves a respirator which has holes in the side of a mask and a cup in front with an opening including valve means having an outlet into the interior of the mask. In U.S. Pat. No. 4,328,797 is described a mask which is adapted to provide for the passage of a tube therethrough. U.S. Pat. No. 5,005,571 involves a mouth nose mask having breathing monitor or the like apparatus mounted on a patient's face independent of a nasal cannula and over the cannula without impeding its function. U.S. Pat. No. 5,046,491 deals with collection and transportation separately or simultaneously of gases inhaled or exhaled via a patient's mouth during anesthesia or the like, using a nasal gas cannula and an oral gas capture member. None of the foregoing art solves the problem of how to monitor the breathing of a patient under anesthesia substantially without discomfort to the patient or problems during monitoring.

SUMMARY OF THE INVENTION

After extended investigation I have found a gas sampling oxygen mask made up simply of securing means for fastening behind the head and a flexible membrane mask, made, for example, of polyvinyl chloride, and shaped for fitting downward over the slight outward angle of the brow of the nose and continuing downward at that angle before turning substantially straight or vertically downward after coming out far enough to leave a breathing pocket or chamber in front of the nostrils and the mouth and then turning horizontally back toward the indentation between lower lip and chin before going straight downward or vertically and then under the chin and upward again in a more or less elliptical manner, counting going up both sides as do the above directions due to the symmetrical shape of the face, that is, both sides being covered by the mask back midway along the cheeks below the eyes. Except for preferred holes or small ports in each side of the nose-cheek portion, the mask has only two openings, one for oxygen intake or inward oxygen breathing via an oxygen intake tube having a female oxygen connector to an oxygen source and the other opening for withdrawing respiratory gas containing carbon dioxide via a bevelled tube continuous with a female luer connector and a sampling transfer tube leading to a gas monitor. The female luer connector is preferably molded integrally with the mask. The oxygen intake line also includes a male connector which is preferably molded integrally with the mask. The two openings are in the floor of the pocket or chamber, that is the part which turns back toward the recess between the chin and the lower lip.

BRIEF DESCRIPTION OF THE DRAWING

For a better understanding of my invention reference will now be made to the drawing, in which, FIG. 1 is a perspective view of the mask of the invention worn by a patient from one side.

FIG. 2 is a perspective view of the mask of the invention worn by a patient seen from the front.

FIG. 3 is a perspective view from one side of the mask of the invention shown on a patient and showing only the parts of the mask involved in carrying the oxygen in and the respiratory gas out and the shape of the mask.

FIG. 4 is a view similar to that of FIG. 3 except for showing the path of respiratory gases as well as come of the incoming oxygen.

DETAILED DESCRIPTION

In the drawing, oxygen mask 10 has an upper nasal portion 12, a breathing space or chamber or pocket 14 and an outer boundary 16 which angles downward along a nose line, continuing along the same nose line downward after passing the tip of the nose, then going vertically downward to the level a point between the lower lip and the chin, then going back inward to form the floor 18 of pocket 14, next downward along and around the chin before finally going back up along the cheeks just behind the nose and mouth to the beginning of upper nasal portion 12. Oxygen from a tank or other source is breathed in via tube 32 and female connector 30, for example, of the slip-on type, and a male connector 20, which may be molded integrally with the mask, in an opening between chin and lower lip level in the bottom 18 of breathing space, chamber or pocket 14 (see arrows). Respiratory gas containing carbon dioxide is breathed out through bevelled tube 24, which has a bevelled intake end 38 (see arrows) and a female luer connector 22 molded integrally with the mask, and continues on through male luer connector 34, which may be of the twist-on variety, from which it proceeds via a tube 36 to a respiratory gas monitor.

It is preferred to have ports or holes 26 on each side of the mask. Also, an elastic band or strap 28 may conveniently be attached to each side of the mask at the rear to fit behind the head when the mask is worn.

In the preferred embodiment, as shown in FIGS 1-4, bevelled end sampling tube 24 extends inside of mask 12 being in front of and having bevelled end 38 adapted to be directed toward the mouth and the nose where the respiratory gas is exhaled.

While the invention has been described in terms of certain preferred embodiments thereof, the claims appended hereto are intended to encompass all embodiments which fall within the scope of the invention.

Having thus described my invention and certain preferred embodiments thereof, I claim:

1. A $CO_2$ gas sampling mask comprising securing means, a mask membrane sufficiently flexible to be held around the cheeks in an elliptical manner by said securing means, said mask when worn by a patient fitting downward from about an eye level starting level along a nose at the nose angle from vertical to a point beyond the tip of the nose and then turning downward to a level about even with an indentation between lower lip and chin to form a floor of a pocket and then going around the chin upward over the cheek and back to said eye level starting level, said mask having two openings in said floor, a forward opening for introduction of oxygen therethrough and a rearward opening for removing respiratory gas to measure carbon dioxide content comprising a bevelled intake end sampling tube molded integrally with said mask and continuous with an integrally molded female luer locking connector, said bevelled end sampling tube extending inside of said mask in front of the mouth and the nose and having said bevelled end adapted to directed toward the mouth and the nose from which respiratory gas is exhaled.

2. The $CO_2$ gas sampling tube of claim 1 wherein said forward opening comprises a male oxygen connector integrally molded with said mask membrane and continuing with an external male oxygen connector.

3. The $CO_2$ gas sampling mask of claim 1 wherein assembled together for breathing oxygen into said mask and on into said nose and mouth and for removing respiratory gas containing carbon dioxide are, going from said openings outward, for oxygen, a male connector, a female connector and a tube for receiving oxygen from a source, and, for removing respiratory gas containing carbon dioxide, said bevelled sampling tube, said female luer connector, a male luer connector, and a respiratory gas transfer tube.

4. The $CO_2$ gas sampling mask of claim 1 wherein said securing means comprise an elastic fastener going around a head proximal ear level continuously from one side of the head to the other.

5. The $CO_2$ gas sampling mask of claim 1 having a plurality of small openings on the cheek portions thereof.

6. An oxygen mask placeable over the nose and mouth of a user comprising:
   a. a pocket;
   b. an inflow tube penetrating said pocket for directing oxygen into said pocket toward the nose and the mouth; and
   c. a sampling tube penetrating said pocket between said inflow tube and the mouth, said sampling tube having a bevelled end opening toward said mouth and away from said inflow tube, said sampling tube extending inside of said mask in front of the mouth and the nose and having said bevelled end adapted to be directed toward the mouth and the nose from which respiratory gas is exhaled.

* * * * *